United States Patent [19]

Brandley et al.

[11] Patent Number: 5,032,679
[45] Date of Patent: Jul. 16, 1991

[54] HEPARIN FRAGMENTS AS INHIBITORS OF SMOOTH MUSCLE CELL PROLIFERATION

[75] Inventors: Brian K. Brandley, Alameda; Lun H. Lam, Cupertino; Roger A. Laine, Alameda, all of Calif.

[73] Assignee: Glycomed, Inc., Alameda, Calif.

[21] Appl. No.: 400,661

[22] Filed: Aug. 31, 1989

Related U.S. Application Data

[63] Continuation-in-part of Ser. No. 285,546, Dec. 15, 1988, abandoned.

[51] Int. Cl.$^5$ .................. C08B 37/00; C07H 5/00; A61K 31/00
[52] U.S. Cl. .................. 536/21; 536/17.2; 536/17.5; 536/17.9; 536/22; 536/124
[58] Field of Search .............. 536/21, 124, 17.2, 17.5, 536/17.9, 22; 514/56, 42

[56] References Cited

U.S. PATENT DOCUMENTS 4,401,662  8/1983  Lormeau et al. .................. 536/21

OTHER PUBLICATIONS

Casu, (1985) "Structure and Biological Activity of Heparin" in Advances in Carbohydrate Chemistry and Biochemistry 43:51-134.
Castellot et al., (1986) Journal of Cell Biology 102:1979-1984.
Benitz et al., (1986) Journal of Cellular Physiology 127:1-7.

Primary Examiner—Ronald W. Griffin
Assistant Examiner—Everett White
Attorney, Agent, or Firm—Irell & Manella

[57] ABSTRACT

A glycosaminoglycoside (GAG) composition predominantly of tetrasacchardie units derived from heparin/heparan sulfate has enchanced activity in preventing the proliferation of smooth muscle cells. This GAG preparation is useful in the treatment of diseases characterized by unwanted smooth muscle cell proliferation and activity.

27 Claims, 3 Drawing Sheets

HEPARIN FRAGMENTS AS INHIBITORS OF SMOOTH MUSCLE CELL PROLIFERATION

This is a continuation in part of U.S. Ser. No. 285,546 filed 15 Dec. 1988 which has been abandoned.

Technical Field

The invention relates to the use of carbohydrate preparations as therapeutic and diagnostic compositions. In particular, the invention relates to a heparin derivative having a molecular weight corresponding to a tetrasaccharide unit to treat diseases and conditions characterized by excessive smooth muscle cell proliferation.

BACKGROUND ART

Proliferation of smooth muscle cells in blood vessel walls occurs in response to vascular injury, and in association with certain disease states (Austin, G. E., et al., *J Am Coll Cardiol* (1985) 6:369-375). The proliferation of these cells can have negative effects due to the production of excess proteins or other matrix molecules, which, along with the cells themselves, form pathologic lesions of, for example, atherosclerosis, renal hypertension, pulmonary hypertension, vasculitis, and postsurgical vascular retinosis. These results are distinguished from the acute response to trauma characterized by blood clotting.

Glycosaminoglycans (GAG) are alternating copolymers of a hexosamine and an aldouronic acid which are found in sulfated forms and are synthesized as proteoglycans. They have collectively been called mucopolysaccharides. To place the compositions discussed below in context, it may be noted that heparin and heparan sulfate are members of the GAG family which are classified by the nature of the hexosamine/aldouronic acid repeating units. For example, in chondroitin sulfates, the aldouronic acid is primarily D-glucuronic acid, and the hexosamine is acetylated 2-amino-2-deoxy-D-galactose (N-acetyl galactosamine, GalNac). In dermatan sulfate (chondroitin sulfate B) the aldouronic acid is mostly L-iduronic acid and the hexosamine is GalNAc. In keratin sulfate, the aldouronic acid is replaced by D-galactose, and the hexosamine is mostly acetylated 2-amino-2-deoxy-D-glucose (N-acetyl glucosamine, GlcNAc). In the compositions of interest herein, heparan sulfate and heparin, the hexosamine is mostly acetylated and sulfated glucosamine ($GlcNH_2$), and the aldouronic acid is mostly L-iduronic in heparin and mostly D-glucuronic acid in heparan sulfate. Heparan sulfate is commonly considered to have a higher proportion of glucuronic acid than heparin.

Problems of heterogeneity in preparations of heparan sulfate or heparin isolated from tissues make sharp distinctions difficult, since these oligosaccharides are related by the biosynthesis pathway, as explained below. Conventional heparin (used as an anti-coagulant) has a molecular weight of 5-25 kd and is extracted as a mixture of various chain lengths by conventional procedures. These procedures involve autolysis and extraction of suitable tissues, such as beef or porcine lung, intestine, or liver, and removal of nonpolysaccharide components.

The molecular weight of the chains in the extract is significantly lower than the 60-100 kd known to exist in the polysaccharide chains of the heparin proteoglycan synthesized in the tissue. The GAG moiety is synthesized bound to a peptide matrix at a serine residue through a tetrasaccharide linkage region of the sequence Xyl-Gal-Gal-D-GlcA-, which is then elongated at the xylose residue with alternate additions of GlcNac and D-glucuronic acid. The polysaccharide sidechains are modified by a series of enzymes which sequentially deacetylate the N-acetyl glucosamine and replace the acetyl group with sulfate, epimerize the hydroxyl at C5 of the D-glucuronic acid residue (to convert it to L-iduronic acid and the GAG chain from the heparan type to a heparin type), sulfate the O-2 of the resulting L-iduronic acid and then sulfate the O-6 of the glucosamine residue. Some of the chains are further sulfated at the O-3 of the glucosamine residue, either at the heparan or heparin stage. This further sulfation is associated with the active site for antithrombin (anticlotting) activity. Other chemically possible sulfation sites are on the O-3 of L-iduronic or D-glucuronic and O-2 of D-glucuronic acid; however, these are seldom found.

Due to their obvious chemical similarity, isolated "heparin" may contain considerable amounts of what might otherwise be classified as heparan sulfate.

There is an extensive art concerning depolymerization of heparin/heparan sulfate chains and separation of products by size. Particularly relevent is the report of Guo, Y. et al., *Anal Biochem* (1988) 168:54-62 which discloses the results of structure determination after the 2,5-anhydromannose at the reducing terminus is reduced to the corresponding 2,5-anhydromannitol.

The following tetrasaccharides were listed specifically by Guo. In these representations, the following abbreviations are used: D-glucuronic acid=GlcA; L-iduronic acid=IdoA; D-glucosamine=$GlcNH_2$; N-acetyl-D-glucosamine=GlcNAc; D-glucosamine N-sulfate=GlcNS; 2,5-anhydromannose=Man(2,5); 2,5-anhydromannitol=ManH(2,5). The location of the O-linked sulfate residues is indicated by "S" and the number of the position of sulfation where the $SO_3R$ residue is linked to oxygen. In the designations below, the alpha and beta anomeric linkages are as those conventionally found in heparin and the indicated D or L configurations as set forth above pertains. The locations of the sulfates are shown below the abbreviation for the sugar to which they apply.

GlcA—GlcNAc—GlcA—ManH(2,5);

IdoA—GlcNAc—GlcA—ManH(2,5);

IdoA—GlcNAc—GlcA—ManH(2,5);
  2S

IdoA—GlcNAc—GlcA—ManH(2,5);
           6S GlcA—GlcNAc—GlcA—ManH(2,5);
           6S IdoA—GlcNAc—GlcA—ManH(2,5);
           6S           3S IdoA—GlcNAc—GlcA—ManH(2,5);
           6S           6S IdoA—RC—IdoA—ManH(2,5);
  2S   6S    2S IdoA—GlcNAc—GlcA—ManH(2,5);
           6S         3S,6S IdoA—RC—IdoA—ManH(2,5);
  6S  2S      6S (RC represents the ring contracted form analagous to ManH(2,5); it is believed this form is formed when the resulting intermediate hemiacetal is reduced.)

The involvement of heparin or heparan sulfate or degradation products thereof in smooth muscle proliferation has been recognized for some time. Heparin and heparan sulfate can slow or arrest the vascular proliferation associated with injury described hereinabove (Clowes, A. W., et al., *Nature* (1977) 265:625-626). The effect of heparan sulfate and heparin on smooth muscle proliferation is also described by Marcum, J. A., et al. in *Biology of Proteoglycan*, Academic Press (1987) pp. 301-343. The inhibition of vascular smooth muscle cell growth by heparin was further described by Castellot, J. J. Jr., al., *J Biol Chem* (1982) 257:11256-11260 and the effect of heparin on vascular smooth muscle cell growth in fetal tissue was described by Benitz, W. E., et al., *J Cell Physiol* (1986) 127:1-7. The effect of heparin as an inhibitor of both pericyte and smooth muscle cell proliferation was shown by Orlidge, A., et al., *Microvascular Research* (1986) 31:41-53, and these authors further showed that chondroitin sulfate, and dermatan sulfate do not have this effect. A review of the effects of heparin and heparan sulfate on the proliferation of smooth muscle cells is in press by Benitz, W. E. in "The Pulmonary Circulation: Normal and Abnormal", Fishman, A. P., ed., University of Pennsylvania Press (1988).

It is not clear by what mechanism these glycosaminoglycans operate, or to what extent they interact with other growth factors such as epithelial and fibroblast growth factors. It has been proposed that a 3-O sulfate on an oligosaccharide of at least 5 sugars is important in this process (Castellot et al., *J Cell Biol* (1986) 102:1979-1984.

It has now been found that an enhanced antiproliferative activity with respect to smooth muscle cells is associated with a smaller oligosaccharide portion of the heparin or heparan sulfate GAGs.

DISCLOSURE OF THE INVENTION

The invention provides a low molecular weight glycosaminoglycan (GAG) composition which has superior specific antiproliferative activity with regard to smooth muscle cells. The existence of this activity in a low molecular weight GAG provides the opportunity for effective pharmaceutical compositions which can be prepared by isolation of the composition from natural sources or, once the precise structure of the GAG is known, synthetically.

Accordingly, in one aspect, the invention is directed to a process to prepare an GAG subunit of heparin/heparan sulfate having antiproliferative activity. The process comprises separating according to size the components of a mixture formed from the virtually complete depolymerization of heparin/heparan sulfate, and recovering the portion corresponding to a molecular weight characteristic of tetrasaccharides. The invention is also directed to the GAG composition so obtained.

In other aspects, the invention is directed to antibodies, including monoclonal antibodies, which are immunospecific for the GAG composition of the invention, and to methods to determine the level of active GAG by reaction with these antibodies. In other aspects, the invention is directed to therapeutic compositions of the GAG preparation or of its antibodies which are useful in regulating smooth muscle cell proliferation.

In still another aspect the invention relates to a method to separate low molecular weight organic salts from their non-dialyzable inorganic salt contaminants which comprises adsorbing the organic salt onto an ion exchange column to the exclusion of the inorganic salt, and eluting with a dialyzable salt.

BRIEF DESCRIPTION OF THE DRAWINGS

FIG. 2-1 and 2-2 each show representative elution profiles of depolymerized heparin preparations chromatographed on a Biogel P2 gel filtration column.

MODES OF CARRYING OUT THE INVENTION

Figure 1:
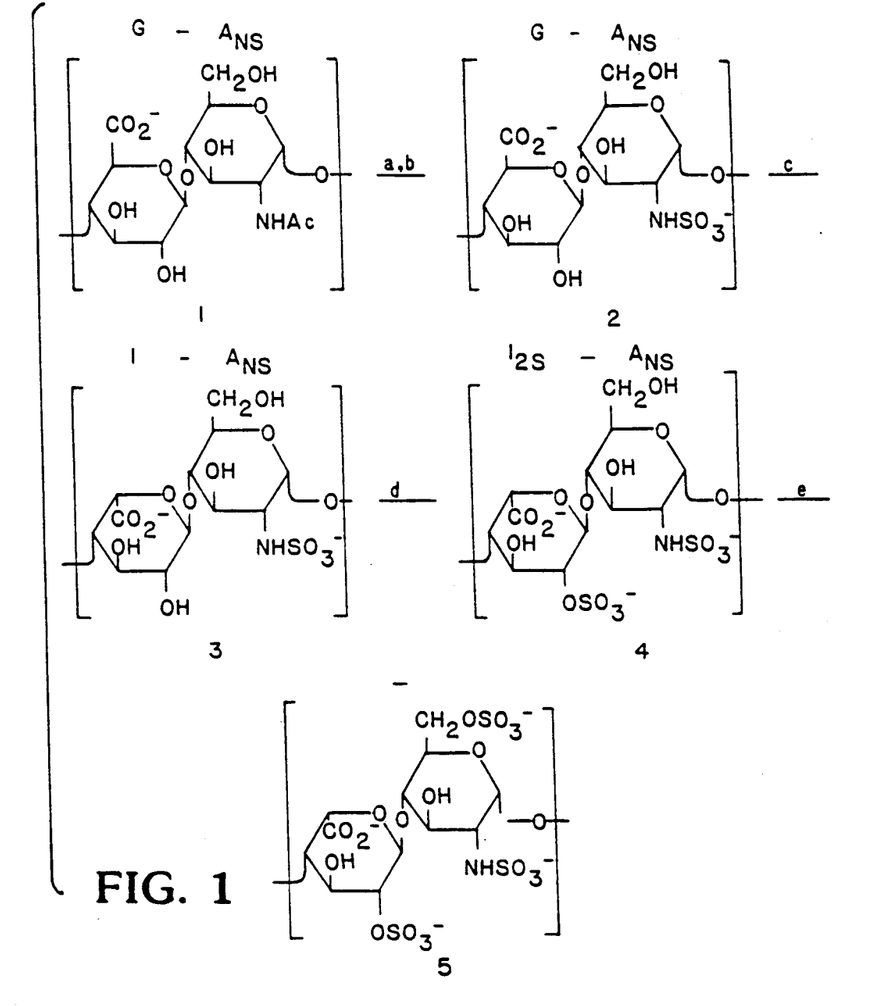
FIG. 1 shows the steps in the biosynthesis of heparan sulfate and heparin and their relationship to each other.

By "heparin/heparan sulfate" is meant a preparation obtained from tissues in a manner conventional for the preparation of heparin as an anticoagulant or otherwise synthesized and corresponding to that obtained from tissue. This preparation may include residues of D-glucuronic acid (GlcA), as characteristic of heparan sulfate as well as iduronic acid (IdoA) as characteristic of heparin. As described in the Background section above, the conversion of D-glucuronic acid to L-iduronic acid is a result of epimerization at the 5 carbon in a heparan-type intermediate. FIG. 1 shows the sequence of steps, and reference to FIG. 1 will clarify this relationship. To the extent that full conversion has not been made, heparan sulfate characteristics remain in the preparation. Because the precise nature of the polymeric chains in the preparations of heparin is not generally determined, and varies from preparation to preparation, the term "heparin/heparan sulfate" is intended to cover the range of mixtures encountered.

The "heparin/heparan sulfate" preparation can be obtained from a variety of mammalian tissues, including, if desired, human tissue. Generally, porcine or bovine sources are used, and vascular tissue is preferred. A preferred source of heparin/heparan sulfate starting material is porcine intestinal mucosa, and preparations labeled "heparin" prepared from this tissue source are commercially available. In general, the heparin/heparan sulfate starting material is prepared from the selected tissue source by allowing the tissue to undergo autolysis and extracting the tissue with alkali, followed by coagulation of the protein, and then precipitation of the heparin-protein complex from the supernatant by acidification. The complex is recovered by reprecipitation with a polar nonaqueous solvent, such as ethanol or acetone or their mixtures, and the fats are removed by extraction with an organic solvent such as ethanol and proteins by treatment with a proteolytic enzyme, such as trypsin. Suitable procedures for the preparation of the heparin starting material are found, for example, in Charles, A. F., et al., *Biochem J* (1936) 30:1927-1933, and modifications of this basic procedure are also known, such as those disclosed by Coyne, E., in *Chemistry and Biology of Heparin*, Elsevier Publisheres, North Holland, N.Y., Lunblad, R. L., et al., eds. (1981).

Preferably, the heparin/heparan sulfate preparation used as a starting material is first purified by extraction with a solvent in which the heparin is insoluble, such as ethanol or acetone. The purified starting material is then depolymerized.

The depolymerization can use various reagents, such as nitrous acid, heparinase or periodate, preferably nitrous acid. The digestion products of the invention correspond to those obtained when nitrous acid digestion is carried to completion under acid conditions. In typcial procedures, the nitrous acid is prepared in situ by solution of sodium nitrate in cold acidic solution at a concentration of 0.01-1.0M, and the reagent is used to treat the heparin at a concentration of 10-100 mg/ml, at a pH of 1-2, preferably 1.5. The reaction is conducted at room temperature, and when complete, can, if desired, be neutralized by addition of a suitable reagent. The complete digestion results in a uniquely constituted mixture of components clearly differing from the results of only partial digestion.

Thus, it is clear that the composition of the various sized fractions of a digestion mixture will depend on the nature and degree of digestion. Depending on the digestion method, the resultant type of cleavage at the linkage cleaved may differ, as well as the locations of cleavage as between, for example, linkages involving L-iduronic acid versus glucuronic acid or linkages between sugars of various levels of sulfation. Accordingly, a predominantly tetrasaccharide mixture retrieved will have a different composition when cleavage is by heparinase than when cleavage is by nitrous acid, and will have a different composition as a result of partial depolymerization as opposed to complete depolymerization.

By "complete depolymerization" is meant a degree of depolymerization which is substantially equivalent to the degree of depolymerization which results from the conduct of the depolymerization process as carried out in the procedure described herein in Example 1. Alternate heparin/heparan sulfate sources may be used, and other depolymerization reagents may be used, so long as the depolymerization results in the components obtained when the digestion is conducted using this procedure and as long as the composition having enhanced antiproliferative activity is obtained.

Thus, other depolymerization methods can be used as long as they produce these active components.

The depolymerization results in a mixture of fragments that can then be separated on the basis of size. A variety of size separation techniques is available, including gel permeation, electrophoresis, and thin layer chromatography, density gradient centrifugation; especially preferred is gel filtration chromatography using a Sephadex or polyacrylamide gel system with a fractionation range of about 100-1800 daltons. A particularly preferred gel permeation resin is Biogel P2, and upon separation using this method, fragments containing disaccharides are effectively separated from those containing tetrasaccharides, hexasaccharides, octasaccharides, and polysaccharides of higher molecular weights.

The size separation can be conducted either before or after the reaction mixture is desalted. It has not previously been possible to effect removal of inorganic ions prior to size fractionation because the dialysis membranes previously available failed to retain the low molecular weight disaccharides and tetrasaccharides obtained in the depolymerization reaction. Accordingly, the salt was removed in the size separation procedure itself, e.g., by elution of the adsorbed materials with volatile solvents such as acetic acid.

It has now been found that inorganic ions may be removed by dialysis prior to size separation, or, in the alternative, salt can be used as an elution medium in the size separation. In part, this possibility is due to the recent availability of dialysis membranes which can separate the tetrasaccharides or disaccharides from ions in the size range of chloride ion. These membranes cannot be used directly because the contaminating ions are sulfate ions and the membranes also retain sulfate—i.e., these membranes are not able to separate sulfate ions from tetrasaccharides. Accordingly, if sulfate ion could be removed from the reaction mixture, and replaced by, for example, chloride ion, dialysis can be utilized to remove these smaller inorganic ions.

This is accomplished by first adsorbing the reaction mixture to an anion exchange resin such as DEAE. This is followed by washing and elution with a low molecular weight salt capable of passing through the dialysis membrane, such as sodium chloride. The eluted fractions can then be dialyzed with the improved membranes. Accordingly, pharmaceutically acceptable compositions are more readily prepared with an efficient means for salt removal.

The fraction containing predominantly tetrasaccharide units shows enhanced activity in inhibiting the proliferation of smooth muscle cells. Verification of this property can be obtained using standard assays, such as those described in Castellot, J. J. Jr., et al., *J Cell Biol* (1986) 102:1979-1984. Other assay methods, such as those of Benitz, W. E., et al., *J Cell Physiol* (1986) 127:1-7 (supra) can also be used.

Compounds of the invention which can be thus obtained are of the formula:

(1)

(2)

wherein n is 0-2, R is H or a cation, X is H or SO₃R, and Ac is acyl (2-5C), preferably acetyl (Ac ), and * indicates that the associated C (carbon 5) can be in either the R or S configuration. Saccharide structures having an odd number of saccharide residues wherein either terminal saccharide is deleted are also included.

In the compounds of formula (2) the sugar at the reducing terminus is deaminated to form the 2,5-anhydromannose shown. When this compound is further reduced, the CHO shown becomes —CH₂OH; however, this reduction does not occur in the depolymerization reaction per se. Forms wherein the non-reducing terminal sugar is in the 4,5-unsaturated form, i.e., may also be included, but do not result from digestion with nitrous acid. Digestion with nitrous acid is specific for cleavage at an N-sulfated glucosamine, therefore complete digestion products of larger chain lengths than disaccharides must contain unsulfated glucosamines.

In particularly preferred embodiments, n is 1. The cations represented by R can either be inorganic cations such as sodium, potassium, calcium, or ammonium ion or can be organic cations such as those obtained from quaternary amines and these salts are formed by simple neutralization.

Representative compounds of the invention, wherein R is as above defined are set forth as follows. In these representations, the following abbreviations are used: D-glucuronic acid=GlcA; L-iduronic acid=IdoA; D-glucosamine=GlcNH$_2$; N-acetyl-D-glucosamine=GlcNAc; D-glucosamine N-sulfate=GlcNS; 2,5-anhydromannose=Man(2,5); 2,5-anhydromannitol=ManH(2,5). The location of the O-linked sulfate residues is indicated by "S" and the number of the position of sulfation where the SO$_3$R residue is linked to oxygen. In the designations below, the alpha and beta anomeric linkages are as those shown in formula 1 above and the indicated D or L configurations as set forth above pertains. The locations of the sulfates are shown below the abbreviation for the sugar to which they apply.

```
GlcA—GlcNAc—GlcA—GlcNS;
GlcA—GlcNAc—GlcA—GlcNS;
                        6S
GlcA—GlcNAc—GlcA—GlcNS;
         6S              6S
GlcA—GlcNAc—GlcA—GlcNS;
                   6S
GlcA—GlcNAc—GlcA—GlcNS;
         3S,6S           6S
GlcA—GlcNAc—IdoA—GlcNS;
         6S              6S
GlcA—GlcNAc—IdoA—GlcNS;
         6S    2S        6S
GlcA—GlcNAc—IdoA—GlcNS;
         6S    2S        3S,6S
GlcA—GlcNAc—IdoA—GlcNS;
               2S        6S
IdoA—GlcNac—GlcA—GlcNS;
IdoA—GlcNac—GlcA—GlcNS;
         6S              6S
IdoA—GlcNAc—GlcA—GlcNS;
2S       6S              6S
IdoA—GlcNac—GlcA—GlcNS;
2S       6S              3S,6S
IdoA—GlcNac—GlcA—GlcNS;
2S                       3S,6S
IdoA—GlcNac—GlcA—GlcNS;
2S       6S
IdoA—GlcNac—IdoA—GlcNS;
2S       6S    2S        3S,6S
IdoA—GlcNAc—IdoA—GlcNS;
IdoA—GlcNAc—IdoA—GlcNS;
2S
IdoA—GlcNAc—IdoA—GlcNS;
2S       6S    2S        6S
IdoA—GlcNAc—IdoA—GlcNS;
2S             2S
IdoA—GlcNAc—IdoA—GlcNS;
2S       6S    2S
IdoA—GlcNac—IdoA—GlcNS;
2S             2S        6S
```

-continued
```
IdoA—GlcNAc—IdoA—GlcNS;
         6S              3S,6S
IdoA—GlcNAc—IdoA—GlcNS;
         3S,6S 2S        6S
IdoA—GlcNAc—IdoA—Man(2,5);
2S       6S    2S        6S
IdoA—GlcNAc—IdoA—Man(2,5);
               2S        6S
IdoA—GlcNAc—IdoA—Man(2,5);
2S             6S
IdoA—GlcNAc—GlcA—Man(2,5);
2S       6S              6S
IdoA—GlcNAc—IdoA—Man(2,5).
         3S,6S 2S        6S
```

Various other levels of sulfation for these representative compounds are also included. In addition, included in the invention, are modified forms of these structures which are disaccharides, trisaccharides, pentasaccharides, and hexasaccharides.

Preparation of Antibodies

The separated composition containing predominantly tetrasaccharide unit fragments can be used to stimulate the production of antibodies which immunoreact with the components of the composition. Standard immunization protocols using this predominantly tetrasaccharide composition in various mammals, such as rabbits, rats, mice, and sheep, result in antisera which are immunoreactive with the composition components. The composition is advantageously conjugated to a suitable antigenically neutral carrier, such as an appropriate serum albumin or keyhole limpet hemocyanin, in order to enhance immunogenicity. Furthermore, the antibody-secreting cells of the immunized mammal can be immortalized to generate monoclonal antibody panels which can then be screened for reactivity with the composition. Techniques for preparation of monoclonal antibodies to heparin oligosaccharides are described by Pejler, G., et al., *J Biol Chem* (1988) 263:5197-5201, incorporated herein by reference.

The resulting polyclonal or monoclonal antibody preparations are useful in assays for levels of active antiproliferative component in biological samples, as described below, as well as in passive therapy to prevent excessive repression of the proliferation of smooth muscle cells.

Statement of Utility

The oligosaccharide composition of the invention, containing predominantly tetrasaccharide fragments, is useful in therapeutic applications for treatment of conditions or diseases which are characterized by excessive and destructive smooth muscle cell proliferation. These conditions frequently occur where the subject has been exposed to trauma, such as in the case of surgical patients. The trauma caused by wounds or surgery results in vascular damage and secondary smooth muscle cell proliferation, which secondary proliferation results in vascular retinosis. This undesirable result can occur after vascular graft surgery, heart transplantation, balloon or laser angioplasty, arterial traumatic injury, post-surgical repair of muscular arteries, long-term in-dwelling of arterial catheters, invasive arterial diagnostic procedures, kidney, lung or liver transplants, coronary artery bypass surgery, carotid artery bypass surgery, femoral popliteal bypass surgery, and intracranial arterial bypass surgery.

In addition to secondary smooth muscle cell proliferation events occurring as a result of trauma, certain diseases are associated with unwanted vascular proliferation, although in these cases, too, it is assumed that some internal unknown injury has caused the secondary result. These disease states include Goodpasture syndrome, acute glomerulonephritis, neonatal pulmonary hypertension, asthma, congestive heart failure, adult pulmonary hypertension, and renal vascular hypertension.

For all these diseases and conditions, administration of suitable amounts of the composition of the invention is useful in treatment. Administration is by typical routes appropriate for polysaccharide compositions, and generally includes systemic administration, such as by injection. Particularly preferred is intravenous injection, as continuous injection over long time periods can be easily continued. Typical dosage ranges are in the range of 0.1-10 mg/kg/hr on a constant basis over a period of 5-15, preferably 7-10, days. Particularly preferred dosage is about 0.5 mg/kg/hr, or, for a 70 kg adult, 35 mg/hr or 840 mg/day.

Other modes of administration are less preferred but may be more convenient. Injection subcutaneously at a lower dose or orally at a slightly higher dose than intravenous injection, or by transmembrane or transdermal or other topical administration for localized injury may also be effective. Localized administration through a continuous release device, such as a supporting matrix, perhaps included in a vascular graft material, is particularly useful where the location of the trauma is accessible.

Formulations suitable for the foregoing modes of administration are known in the art, and a suitable compendium formulations is found in *Remington's Pharmaceutical Sciences*, Mack Publishing Company, Easton, Pa., latest edition.

The composition of the invention may also be labeled using typical methods such as radiolabeling, fluorescent labeling, chromophores or enzymes, and used in a competitive assay for the amount of antiproliferative component in a biological sample. Suitable protocols for competitive assays of analytes in biological samples are well known in the art, and generally involve treatment of the sample, in admixture with the labeled competitor, with a specific finding partner which is reactive with analyte such as, typically, an immunoglobulin or fragment thereof. The antibodies prepared according to the invention are useful for this purpose. The binding of analyte and competitor to the antibody can be measured by removing the bound complex and assaying either the complex or the supernatant for label. The separation can be made more facile by preliminary conjugation of the specific binding partner to a solid support. Such techniques are well known in the art, and the protocols available for such competitive assays are too numerous and too well known to be set forth in detail here.

The antibodies of the invention are useful in immunoassays, not only of the type described above involving competition between labeled composition and the analyte antiproliferation factor in the sample, but also for direct immunoassay for the factor. Alternate protocols involving direct assays are also of wide variety and well known. Typically, the analyte bound to antibody is detected by means of an additional reactive partner which bears a label or other means of detection. Thus, in typical sandwich assays, for example, the binding of the antibodies of the invention to analyte can be detected by further reaction with a labeled preparation of these same antibodies or by labeled antibody immunoreactive with this preparation by virtue of species differences.

The antibodies of the invention can also be formulated into pharmaceutical compositions and used to stimulate the growth of smooth muscle cells in subjects for which this result is desirable.

The following example is intended to illustrate but not to limit the invention.

EXAMPLE 1

Preparation of the Predominantly Tetrasaccharide Composition

Commercial porcine intestinal mucosa heparin was dissolved in 1 M NaCl to approximately 270 mg/ml, and then precipitated by addition of 3 volumes of 95% ethanol. The precipitated heparin was centrifuged at 3,000×g and the pellet recovered and redissolved and reprecipitated as described for an additional 2 precipitations. The final heparin pellet was then lyophilized.

To prepare the nitrous acid reagent, sodium nitrite was dissolved in ice cold 0.24M citric acid to obtain a 0.06M solution of $IO_2^-$. 5 parts of the nitrous acid reagent was then added to 1 part of a 300 mg/ml heparin solution. The preparation was allowed to come to room temperature, titrated to pH 1.5 with 1M $H_2SO_4$ and allowed to react for 1 hr at 30° C. The reaction was quenched by addition of ammonium sulfamate to 0.5M.

The resulting depolymerized heparin was then applied to a 2.5×97 cm Biogel P2 gel filtration column packed in 15% v/v acetic acid. Elution with 15% v/v acetic acid was continued, and fractions were collected. The concentration of uronic acids in each fraction was determined using the carbazole assay of Bitter, T., et al., *Anal Biochem* (1962) 4:330.

Figure 21:
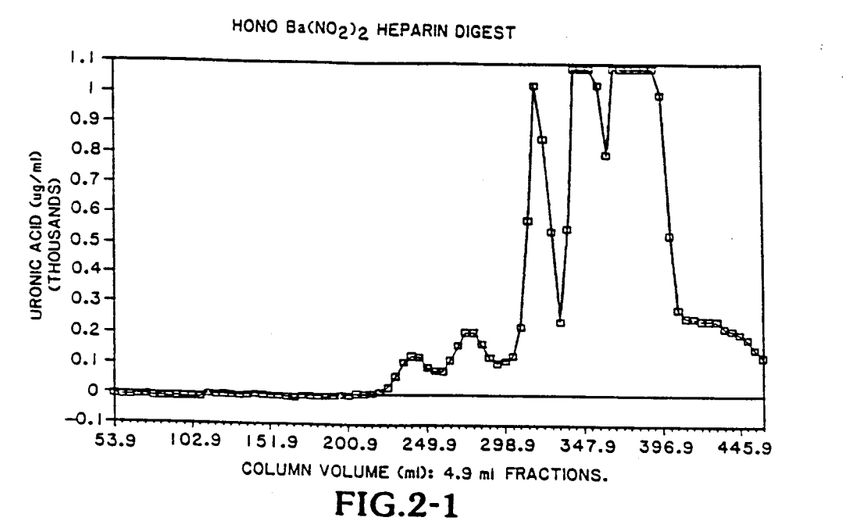
Figure 22:
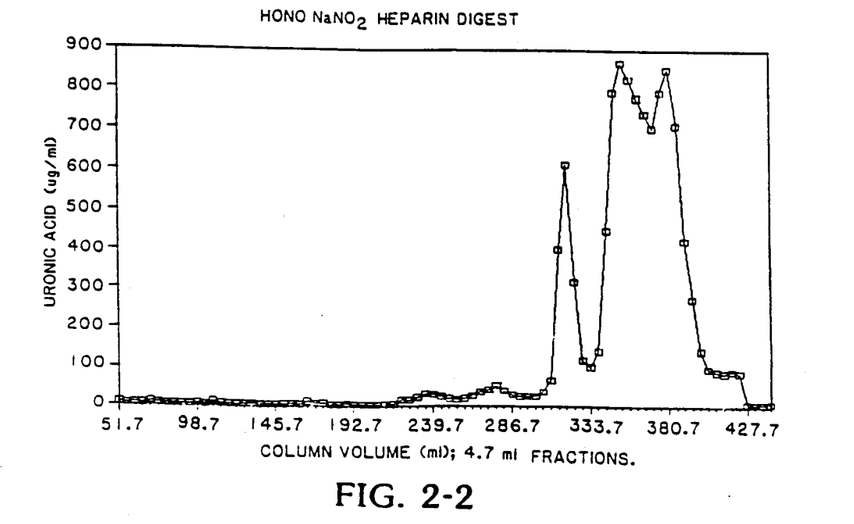

Typical elution profiles are shown in FIG. 2. The peak elution at approximately 320 ml ($V_e/V_o = 0.67$) contains mostly tetrasaccharides.

The fraction containing the tetrasaccharide-predominating mixture is then lyophilized for storage.

EXAMPLE 2

Effect on Smooth Muscle Proliferation

Solutions to be tested were made up in "complete medium", which is DMEM medium containing 10% fetal calf serum and penicillin/streptomycin.

Bovine smooth muscle cells (SMC) were isolated from bovine pulmonary artery by the method of Benitz, W. E., et al., *J Cell Physiol* (1986) 127:1-7. SMC from passage 3-10 were plated at 350-700 cells per well in 96-well microtiter plates in the medium above and allowed to attach for 2-4 hr. The complete medium was replaced with DMEM supplemented with 0.1% fetal calf serum, and the cells were incubated for an additional 72 hr to arrest cell growth. The low-serum medium was then replaced with complete medium containing the test samples.

The cells were allowed to grow for up to 7 days with replicate plates sampled at regular intervals. Cell number was determined by removing the medium and washing the cells with phosphate-buffered saline, adding 75-150 ul lysis buffer, and assaying for lactate dehydrogenase (LDH) activity, as described by Brandley, B., et al., *J Biol Chem* (1987) 262:6431. The activity of LDH is proportional to cell number.

Figure 3:
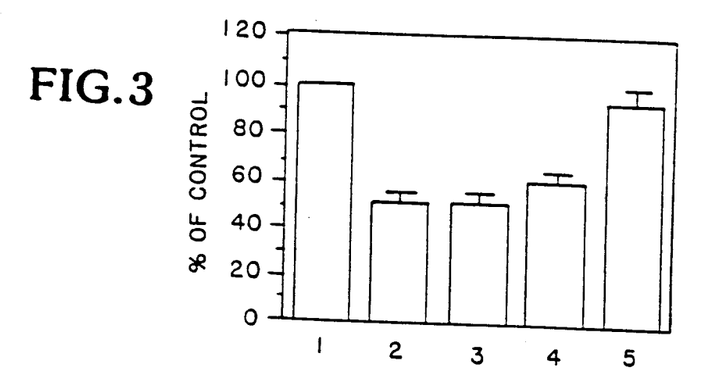
FIG. 3 shows the antiproliferative activity of the compositions of the invention in an in vitro assay.

The results of one such assay are shown in FIG. 3. Bars #1 and #5 are controls. Bar #1 contains no GAG. Bar #5 represents a test solution of 150 ug/ml chondroitin sulfate. Bar #4 contains 150 ug/ml of commercial heparin. Bars #2 and #3 contain the composition of the invention at 50 ug/ml. The ability of the invention composition to inhibit the proliferation of growth exceeds that of commercial heparin.

At 60 ug/ml, the composition of the invention as prepared in Example 1 inhibits growth of SMC 90%, as compared to controls; at 6.6 ug/ml, it inhibits growth of SMC to a level equal to that obtained with 150 ug/ml heparin, or by 50%.

A second preparation of the invention composition inhibited SMC growth 50% at concentrations of 10–100 ug/ml.

We claim

1. A process to prepare a glycosaminoglycoside (GAG) composition useful in preventing or inhibiting the proliferation of smooth muscle cells which method comprises:
   separating a mixture obtainable by complete nitrous acid depolymerization of mammalian heparin/heparan sulfate into fragments according to molecular size, and
   recovering the size fraction of the mixture comprised predominantly of fragments which are tetrasaccharide units, the mixture of fragments having a lower antithrombotic activity and a higher activity for inhibiting the proliferation of smooth muscle cells as compared with commercial heparin.

2. The process of claim 1 wherein the heparin/heparan sulfate is depolymerized with nitrous acid.

3. The process of claim 1 wherein the depolymerized fragments are separated using gel filtration.

4. The process of claim 3 wherein gel filtration is conducted using a column containing Biogel P2, and eluting with 15% V/V acetic acid.

5. A GAG composition prepared by the process of claim 1.

6. The GAG composition of claim 5 conjugated to label.

7. A pharmaceutical composition useful in the treatment of conditions characterized by unwanted smooth muscle cell proliferation, which composition comprises an effective amount of the GAG composition of claim 5 in admixture with at least one pharmaceutically acceptable excipient.

8. A method to treat a condition characterized by unwanted smooth muscle cell proliferation, which method comprises administering to a subject in need of such treatment an effective amount of the composition of claim 5 or a pharmaceutical composition thereof.

9. The method of claim 8 wherein the condition is a result of surgery or trauma.

10. The method of claim 8 wherein the condition is selected from the group consisting of Goodpasture's syndrome, acute glomerulonephritis, neonatal pulmonary hypertension, asthma, acute pulmonary hypertension and renal vascular hypertension.

11. The method of claim 8 wherein the composition is administered intravenously.

12. The method of claim 9 wherein the composition is administered topically or at the location of trauma.

13. A method to diagnose a deficiency or excess in antiproliferative oligosaccharides in a mammalian subject which method comprises assessing in a biological sample taken from the subject the level of oligosaccharide competitive in an immunoassay with the composition of claim 5 in labeled form.

14. A compound obtainable by isolation from depolymerized heparin which is a hexasaccharide or tetrasaccharide, or salt thereof, capable of preventing or inhibiting the proliferation of smooth muscle cells, the compound having a lower antithrombotic activity and a higher activity for inhibiting the proliferation of smooth muscle cells as compared with commercial heparin, wherein the compound has the following structural formula:

(1)

wherein n is 1 or 2, R is H or a cation, X is H or SO$_3$R and Ac is acyl (2–5C), and * indicates that the associated C (carbon 5) can be in either the R or S configuration.

15. The compound of claim 14 wherein n=1.

16. The compound of claim 14 which is selected from the group consisting of:

```
GlcA—GlcNAc—GlcA—GlcNS;

GlcA—GlcNAc—GlcA—GlcNS;
                        6S

GlcA—GlcNAc—GlcA—GlcNS;
              6S        6S

GlcA—GlcNAc—GlcA—GlcNS;
              6S

GlcA—GlcNAc—GlcA—GlcNS;
             3S,6S      6S

GlcA—GlcNAc—IdoA—GlcNS;
              6S        6S

GlcA—GlcNAc—IdoA—GlcNS;
              6S  2S    6S

GlcA—GlcNAc—IdoA—GlcNS;
              6S  2S    3S,6S

GlcA—GlcNAc—IdoA—GlcNS;
                  2S    6S

IdoA—GlcNac—GlcA—GlcNS;

IdoA—GlcNac—GlcA—GlcNS;
              6S        6S

IdoA—GlcNAc—GlcA—GlcNS;
 2S           6S        6S

IdoA—GlcNac—GlcA—GlcNS;
 2S           6S        3S,6S

IdoA—GlcNac—GlcA—GlcNS;
 2S                     3S,6S

IdoA—GlcNac—GlcA—GlcNS;
 2S           6S

IdoA—GlcNac—IdoA—GlcNS;
 2S           6S  2S    3S,6S

IdoA—GlcNAc—IdoA—GlcNS;

IdoA—GlcNAc—IdoA—GlcNS;
 2S

IdoA—GlcNAc—IdoA—GlcNS;
 2S           6S  2S    6S

IdoA—GlcNAc—IdoA—GlcNS;
 2S               2S

IdoA—GlcNAc—IdoA—GlcNS;
 2S           6S  2S
```

-continued

IdoA—GlcNac—IdoA—GlcNS;
2S        2S        6S IdoA—GlcNAc—IdoA—GlcNS;
6S              3S,6S IdoA—GlcNAc—IdoA—GlcNS.
3S,6S     2S     6S 17. The compound isolable from digested heparin which compound has a higher activity for preventing or inhibiting the proliferation of smooth muscle cells and a lower antithrombotic activity as compared with commercial heparin, which compound has the formula:

(2)

wherein n is 1 or 2, R is H or a cation, X is H or SO₃R and Ac is acyl (2-5C) and * indicates that the associated C (carbon 5) can be in either the R or S configuration.

18. The compound of claim 17 wherein the reducing or non-reducing terminal sugar is deleted.

19. The compound of claim 17 wherein n=1.

20. The compound of claim 17 which is selected from the group consisting of:

IdoA—GlcNAc—IdoA—Man(2,5);
2S       6S     2S     6S -continued IdoA—GlcNAc—IdoA—Man(2,5);
                     2S     6S IdoA—GlcNAc—IdoA—Man(2,5);
2S               6S IdoA—GlcNAc—GlcA—Man(2,5);
2S       6S        6S IdoA—GlcNAc—IdoA—Man(2,5).
3S,6S     2S     6S 21. A pharmaceutical composition useful in the treatment of conditions characterized by unwanted smooth muscle cell proliferation, which composition comprises an effective amount of the compound of claim 14 in admixture with at least one pharmaceutically acceptable excipient.

22. A method to treat a condition characterized by unwanted smooth muscle cell proliferation, which method comprises administering to a subject in need of such treatment an effective amount of the compound of claim 14 or a pharmaceutical composition thereof.

23. The method of claim 22 wherein the condition is a result of surgery or trauma.

24. The method of claim 23 wherein the compound is administered topically or at the location of trauma.

25. The method of claim 22 wherein the compound is administered intravenously.

26. The method of claim 22 wherein the condition is selected from the group consisting of Goodpasture's syndrome, acute glomerulonephritis, neonatal pulmonary hypertension, asthma, actue pulmonary hypertension and renal vascular hypertension.

27. A method to diagnose a deficiency or excess in antiproliferative GAG in a mammalian subject which method comprises assessing in a biological sample taken from the subject the level of GAG competitive in an immunoassay with the compound of claim 14 in labeled form.

* * * * *

UNITED STATES PATENT AND TRADEMARK OFFICE
CERTIFICATE OF CORRECTION

PATENT NO. : 5,032,679
DATED : July 16, 1991
INVENTOR(S) : Brian K. Brandley, et al.

It is certified that error appears in the above-indentified patent and that said Letters Patent is hereby corrected as shown below:

The sheets of drawings, consisting of figures 1-3, should be added as shown on the attached pages.

Signed and Sealed this

Nineteenth Day of April, 1994

Attest:

BRUCE LEHMAN

*Attesting Officer*

*Commissioner of Patents and Trademarks*